United States Patent [19]

Chrastil

[11] Patent Number: 5,550,630

[45] Date of Patent: Aug. 27, 1996

[54] SPECTROPHOTOMETRIC METHOD FOR STRUCTURAL ANALYSIS OF ORGANIC COMPOUNDS, POLYMERS, NUCLEOTIDES AND PEPTIDES

[75] Inventor: Joseph Chrastil, Kenners, La.

[73] Assignee: The United States of America as represented by the Secretary of Agriculture, Washington, D.C.

[21] Appl. No.: 34,919

[22] Filed: Mar. 19, 1993

[51] Int. Cl.$^6$ .............................. G01J 3/00; G01J 3/42; G01J 3/427

[52] U.S. Cl. .................. 356/300; 356/319; 356/320

[58] Field of Search .............................. 356/300, 319, 356/320

[56] References Cited

U.S. PATENT DOCUMENTS

| | | | |
|---|---|---|---|
| 3,661,462 | 5/1972 | Natens | 356/51 |
| 3,813,168 | 5/1974 | Honkawa | 356/97 |
| 3,887,281 | 6/1975 | Kurita et al. | 356/96 |
| 3,972,627 | 8/1976 | Rabl et al. | 356/339 |
| 4,781,456 | 11/1988 | Nogami | 356/51 |
| 4,805,623 | 2/1989 | Jöbsis | 128/633 |
| 5,093,271 | 3/1992 | Yamamoto | 436/518 |
| 5,216,487 | 6/1993 | De Bruin et al. | 356/443 |
| 5,242,602 | 9/1993 | Richardson et al. | 356/300 |
| 5,245,418 | 9/1993 | Gilmour et al. | 356/443 |
| 5,255,069 | 10/1993 | Duarte | 356/443 |
| 5,296,843 | 3/1994 | Wohlstein et al. | 340/603 |
| 5,359,681 | 10/1994 | Jorgenson et al. | 385/12 |
| 5,371,020 | 12/1994 | Frischaf | 436/165 |

OTHER PUBLICATIONS

Chrastill, Joseph, "A Group Additivity Model for Analyzing Absorption Spectra of Organic Compounds: Applications to Partial Structural Analysis and Molecular Weight Determinations of Polymers, Nucleotides, and Peptides", *Analytical Biochemistry*, 202, 1992, pp. 126–145.

Primary Examiner—Rolf Hille
Assistant Examiner—David Ostrowski
Attorney, Agent, or Firm—M. Howard Silverstein; Randall E. Deck; John D. Fado

[57] ABSTRACT

A method for analyzing the structures of chemical organic compounds, polymers, polynucleotides and peptides is disclosed. The method uses the integrated intensity of spectral light absorption in wide or narrow regions of the ultraviolet and/or visible spectrum and relates these parameters additively to the structural characteristics of the analyzed chemical compound. For the analysis of polymers, nucleotides and/or peptides the integrated intensities of spectral absorption are used sequentially in narrow regions of the ultraviolet light which enables the determination of the molecular weight and the complete amino acid composition of the analyzed compound. All these procedures are interconnected in an automatic spectrophotometric structural analyzer.

8 Claims, 1 Drawing Sheet

5,550,630

SPECTROPHOTOMETRIC METHOD FOR STRUCTURAL ANALYSIS OF ORGANIC COMPOUNDS, POLYMERS, NUCLEOTIDES AND PEPTIDES

BACKGROUND OF THE INVENTION

1. Field of the Invention

The invention relates to a method for the determination of the molecular weight and structure of organic compounds, synthetic or natural polymers, polynucleotides and polypeptides from their absorption spectra.

2. Description of the Prior Art

The absorption peaks or their shifts in visible or ultraviolet light can generally only rarely be used for the determination of chemical structure because they are irregular and unpredictable. Also the chemical substitutions in aliphatic chains or aromatic rings very often cause irregular shifts of absorption peaks and another approach to this problem is needed.

There is presently no simple general single method for polymer analysis. Several more or less complicated methods must be used in order to reveal the molecular weight and the composition of the studied polymer. For example, the nucleotide and/or amino acid analyzers are based on a complete nucleotide or peptide hydrolysis by strong acids or alkalis. This is laborious and causes many problems.

In one such analysis, during hydrolysis part of the carbohydrate from nucleotides or several amino acids from peptides (i.e. tryptophan, asparagine, glutamine and cysteine) are completely destroyed, while others (i.e. serine, threonine) are partially destroyed. The analysis of the remaining nucleic bases or amino acids in the hydrolysate is also accompanied by relatively large errors. Thus these results are not very reliable and reproducible. Additionally, a relatively large amount of the sample is needed and the analyzed sample is completely lost.

The additivity of chemical group contributions has been found with different physicochemical properties of organic compounds, for example, parachor, molecular refractivity, or optical rotation. This approach has not been applied to the uv or vis absorption spectral peaks in any great detail. The reason is obviously because the absorption peaks are broad, do not confine to a single wavelength, and extend over wide regions. In contrast to their spectra, the positions of the peaks of the absorbing chemical groups are not accurately predictable because of the unpredictable excited states.

Although several sets of empirical rules have been established (for example, Woodward's or Fieser's rules for the maxima or dienes or dienones), the maxima are generally only poorly related to the structure. Chain or aromatic ring substitutions create more or less irregular absorption shifts to longer or shorter wavelengths and tautomery invalidates most of the empirical rules. This is the main reason why the visible and ultraviolet absorption maxima can only rarely be used for the qualitative identification and/or quantitative determination of chemical structural characteristics.

SUMMARY OF THE INVENTION

We have now discovered that the molecular weights and/or structures of chemical compounds may be determined from their UV or visible spectra based upon the integrated intensity of light absorption. The process may be used to determine the molecular weights and structures of a variety of chemical compounds, including organic compounds, synthetic and natural polymers, polynucleotides and polypeptides. Using this method, pure or substantially pure samples of the chemical to be analyzed are provided in a spectrophotometer, a light beam at a first wavelength $\lambda$ passed therethrough, and the absorbance of the sample at that wavelength measured. These absorbance measurements are repeated at a plurality of different wavelengths to obtain the absorption spectra of the compound over a wide or narrow region of the UV or visible spectrum. The spectrosum, described in detail hereinbelow, may be determined from the absorption spectra of the compound, and the structure and/or molecular weight subsequently determined from this spectrosum.

In accordance with this discovery, it is an object of this invention to provide a method and apparatus for the determination of the molecular weight and/or structure of chemical compounds.

It is also an object of the invention to provide a method for this determination which utilizes relatively small volumes of sample and further wherein the sample is not destroyed.

It is yet another object of this invention to provide a method for the determination of the structure of chemical compounds which does not require reaction of the compounds such as by hydrolysis or derivitization.

These and other object and advantages of this invention will become readily apparent from the ensuing description.

Figure 1:
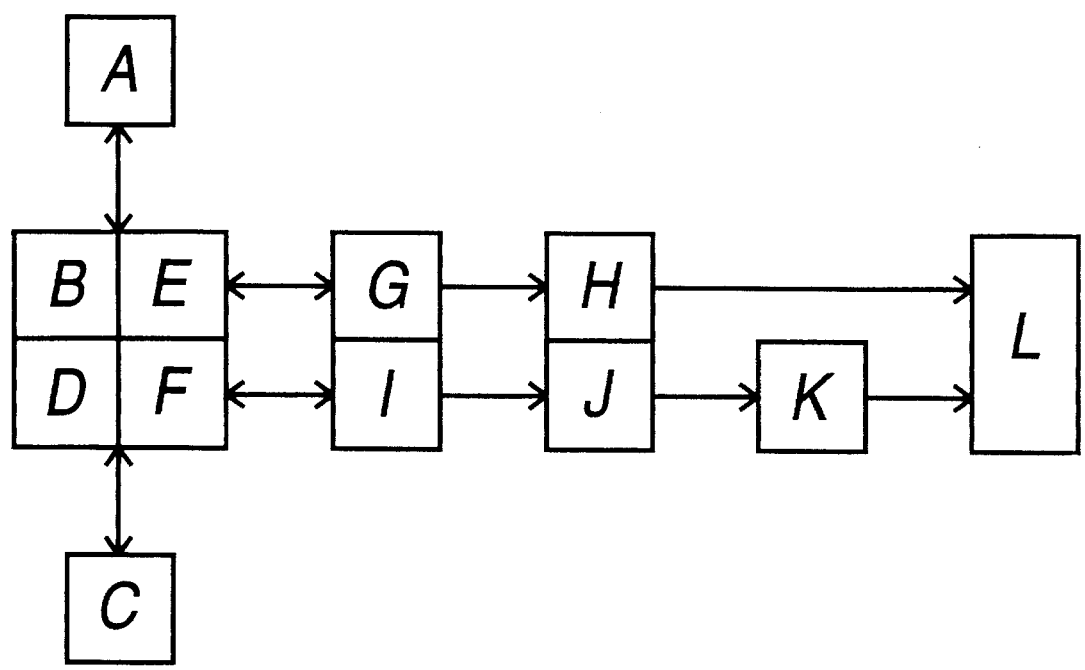
FIG. 1 shows one preferred apparatus for the analysis of samples in accordance with this invention wherein the components are as follows.

A—Spectrophotometer,

B—Automatic cuvette changer,

C—Video monitor,

D—Scanning recorder,

E—Computer hardware for input information,

F—Computer hardware for automatic control of the cuvette holder,

G—Computer hardware for choice of different chemical compound categories,

H—Computer hardware for integration of absorption curves,

I—Computer hardware for printout of spectrosum analysis,

J—Computer hardware for sequential analysis of different polymers, polynucleotides or polypeptides, K—Computer hardware for printout of sequential analytical results, L—Printer.

DETAILED DESCRIPTION OF THE INVENTION

The process of this invention is described in J. Chrastil, A Group Additivity Model for Analyzing Absorption Spectra of Organic Compounds: Applications to Partial Structural Analysis and Molecular Weight Determinations of Polymers, Nucleotides, and Peptides, Analytical Biochemistry, 202:126–145 (April 1992), the contents of which are incorporated by reference herein.

Molecular weights and/or structures of a variety of chemical compounds may be determined using the invention, including organic compounds, natural or synthetic polymers, polynucleotides and polypeptides. Organic compounds particularly suited for analysis by this process include monomeric organic compounds, such as aliphatic, cyclic or aromatic hydrocarbons, which may be branched or straight chain, saturated or unsaturated, and which may be optionally substituted at one or more locations with halogens, oxygen, nitrogen, sulfur or combinations thereof.

When a solution of a chemical compound in a spectrophotometric cuvette absorbs light then $$\frac{N_e}{N_u} = \frac{E}{E - E_a} = \epsilon, \qquad [1]$$

where, E is the energy of photons entering the cuvette, Ea the energy absorbed, $N_e$, the number of excited molecules, $N_u$ the number of unexcited molecules, and $\epsilon$ an extinction coefficient (absorptivity). When E is expressed per square centimeter and N per cubed centimeter, Eq. [1] becomes an intensity equation.

The energy of photons is proportional to the frequency, $v$, and thus, when, E is a unit of energy and a is a constant, we get $$\epsilon = \frac{1}{1 - \alpha v} \qquad [2]$$

The integrated intensity of absorbance at frequency $v$ is $\int_0^v \epsilon dv$ and the integrated intensity of absorbance over the defined range of wavelengths, $\lambda$, is $$I_{\lambda,v} = \int_{\lambda_1}^{\lambda_2} \int_0^v \epsilon dv d\lambda = \int_{\lambda_1}^{\lambda_2} \int_0^v \frac{dv}{1 - \alpha v} d\lambda \qquad [3]$$

In order to increase relative differences between two absorption curves and increase sensitivity, equation [3] was modified, and integration limits on the extinction coefficient, $\epsilon$, were defined by using an arbitrary constant, q. Under these conditions the result is an integral defined herein as the spectrosum:

$$S_\Sigma = \int_{\lambda_1}^{\lambda_2} f_\lambda (\log \epsilon - q) d\lambda. \qquad [4]$$

The wavelengths and value of the constant are not critical and may be selected by the skilled practitioner. Without being limited thereto, for organic compounds $\lambda_1$ may be about 200 rm, $\lambda_2$ may be about 800 and q equal to 2 are preferred. Preferred values for polymers, polynucleotides and polypeptides are described hereinbelow. Using these values for organic compounds, the spectrosum may be readily determined from the absorption spectra for a test compound (plotted as log $\epsilon$ vs. wavelength) as the integrated surface above log $\epsilon=2$ from 200 to 800 rm.

Once the spectrosum has been determined, the structure and molecular weight of the compound may be calculated by virtue of the additive relationship of the spectrosum to the different structural groups, called spectrochromes, which comprise the test compound. The spectrosum is related to the spectrochromes by the equation:

$$S_\Sigma = \Sigma K s_i \cdot n_i \qquad [4.1]$$

where $Ks_i$ are the spectrochrome or structural group constants, and $n_i$ may be determined from the spectrochromes or groups in the test compound. The group constants, $Ks_i$, may be determined from the absorption spectra of known compounds. The different structural groups and their respective constants for use in this invention are shown in Table 1.

The evaluation of a known or potential or suspected structure of a chemical compound using Table 1 is simple. For example, a compound which contains two benzene rings, one nitro group bound to a conjugated (aromatic) ring, one azo (N=N) group bound to two conjugated (aromatic) rings, and one nonconjugated (C=C) group in a side chain will have a spectrosum 2×0.8+1.2+3.3+0.5=6.6 (in [100 rm×log $\epsilon$] units). Alkyls (R) or other groups not included in brackets may contain other groups (for example, halogen) that must be counted separately. The binding sides are apparent from the free valencies of the additive groups.

Conjugated rings do not always represent aromatic rings. For example, the additive constant of cyclotetraene, which does not have aromatic properties was the same as that of benzene. The constants of ortho, meta, and para substituents were almost equal. The difference between the spectrosums of the cis and trans compounds was usually small (0 to ±0.2 in spectrosum units) and this influence was neglected here. Additive constants [10], [26], [33], [36], [37], [45], and [50] were zeros. If there is a choice between two possible cases, for example, in Ph—CH=N—CH=CH—R (Ph is a phenyl and R is an alkyl), group VII is used preferably before other groups and thus the spectrosum of that compound will be 1×1.0(40)+1×0.5(42)+1×0.8(8)=2.3 but not 1×0.8(8)+1×1.0(18)+1×1.0(40)=2.8.

The agreement with all studied compounds was very good. Several typical examples (the number in parentheses is the additive group number from Table 1) are shown in Table 2.

For the determination of the structure of a test compound, the experimentally determined value of the spectrosum may be compared with the groups of Table 1 to exclude any structures having a constant greater than the spectrosum. The spectrosum of possible or suspected structures may also be calculated from the Table for comparison with the experimental value, and structures having calculated spectrosums not closely matching the experimental value may be quickly eliminated from consideration. The determination of the structure is often facilitated when the spectral data is supplemented with additional physical and/or chemical properties which may be used to further characterize the compound. Such properties include but are not limited to reactivity, boiling/melting points, density and solubility, and particularly the molecular formula, which may be determined using techniques conventional in the art. Having the molecular formula of the test compound in hand, possible structures having the same molecular formula may be readily determined, their corresponding spectrosums calculated, and these compared with the experimental value. The structure of the test compound would then correspond to that structure having a closely matching spectrosum. For example, the elemental analysis shows that the studied compound has a formula $C_{10}H_7NO_2$. The spectrosum measured in alcoholic solution is 3.3. This result automatically excludes many possible structures with the same elemental formulas (aminonaphthoquinones (spectrosums =3.9), quinolinecarboxylic acids (spectrosums=2.1), N-phenylmaleimide and nitronaphthalenes (spectrosums=2.8), cyanbenzoylacetaldehydes (spectrosums=2.5), phenylcyanacrylic aids, cyancinnamic acids, nitril of 2-carboxycinnamic acid, and N-vinylphthalimid (spectrosums=2.3), quinolincarboxylic acids (spectrosums=2.1) isochromancarbonitrils and 2-hydroxyacetonitrilbenzofurans (spectrosums=1.6) or 3-cyanmethylphthalid (spectrosum=1.3). On the other hand the spectrosum 3.3 agrees with the formulas of nitrosonaphthols. In a similar manner we can study and confirm the chemical structures of other organic compounds.

The existence of tautomeric forms of organic compounds and the formation of mesomeric resonance systems in solutions that change the free energies of these systems have been previously described. The mesomeric and/or tautomeric equilibria can be readily studied using the present invention. For example, Acetylacetone exists in a mesomeric equilibrium between three keto and enol forms: $CH_3$—CO—$CH_2$—CO—$CH_3 \rightleftharpoons CH_3$—C(CH)=CH—CO—$CH_3 \rightleftharpoons CH_3$—C(CH)=CH—C(OH)—$CH_2$. The first mesomer has spectrosum 1.0, the second 1.5, and the third 2.0. By measuring the spectrosums of acetylacetone in different solvents, the mesomeric equilibria may be obtained. The results are in very good agreement with the bromometric titration of enol (Table 3).

Additional examples of the ability to determine the existence of forms of other chemicals have been demonstrated. For instance, the spectrosums of the p-nitrophenol solutions at different pH ($5\times10^{-6}$M in 0.2M McIlvaine buffers) have shown that it exists in two forms:

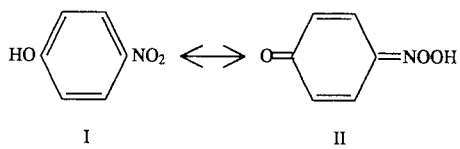

($S_\Sigma=2.5$ and $S_\Sigma=5.5$, respectively). The equilibria of these forms at different pH are shown in Table 4. Similarly, the spectrosums of methyl orange solutions at different pH ($5\times10^{-6}$M in 0.2M McIlvaine buffers) have shown that it exists in two forms:

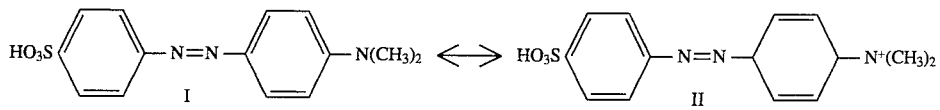

($S_\Sigma=5.1$ and $S_\Sigma=8.7$, respectively). The equilibria of these forms at different pH are shown in Table 5. Finally, the spectrosums of pelargonidine chloride at different pH ($1\times10^{-4}$M in 0.25 ml of 90% ethanol+4.75 ml of 0.2M McIlvaine buffer) have shown that it exists in two forms:

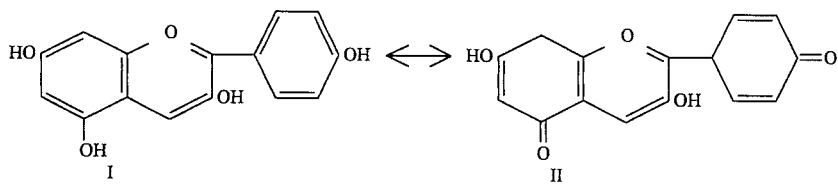

($S_\Sigma=4.6$ and $S_\Sigma=7.2$, respectively). The equilibria of these forms are shown in Table 6. Below pH 1.5 and above pH 13 an irreversible degradation was found (fast decrease to $S_\Sigma=4.3$).

The spectrosums have also proven that some compounds evidently existed in water or ethanol solutions in an equilibrium of two or more tautomeric forms. For example, 4-nitroaniline had an experimental spectrosum in ethanol of $S_\Sigma=3.7$. The spectrosum of structure I,

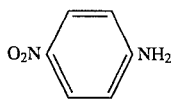

is 2.6 and that of structure II,

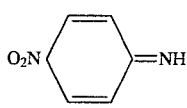

is 3.8, and thus the equilibrium of these two tautomeric structures of 4-nitroaniline in ethanol was close to structure II.

Another example is the tautomeric equilibrium of 2-hydroxy-N-(2-hydroxybenzylidene) aniline. The equilibrium of three tautomeric structures is possible:

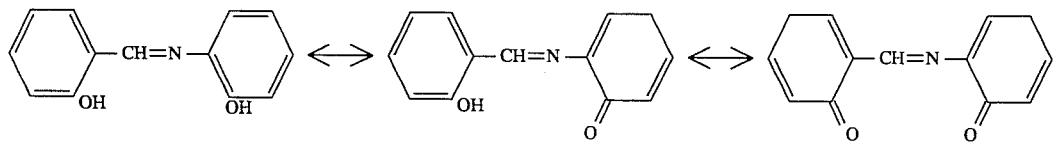

The spectrosums of the first, second, and third structures would be 4.1, 5.4, and 6.7, respectively. Because the experimental spectrosum in ethanol was 5.0, the equilibrium was determined to be between the two extreme left and right structures.

Some molecules such as polymers, polynucleotides, and polypeptides are composed sequentially from a set of similar or same structural units (monomers, nucleotides or amino acids) and the units in these classes of chemical compounds were also additively related to the spectrosums. If the structural units which may be present in the molecule are known (i.e. the monomers of a polymer) and the relationships are not congruent it is possible to determine the composition of these compounds from their sequential integrals in narrow spectral regions. For polynucleotides and polypeptides, the possible structural units are known and encompass the known nucleotides and amino acids, respectively.

By this definition, for example, the integrals [4] for small 1-nm regions ($Ss_\lambda$) are $$Ss_\lambda = \int_{\lambda_i}^{\lambda_{i-1}} f_\lambda(\log \epsilon_\lambda - q)d\lambda \approx (\log \epsilon_\lambda - q)\Delta\lambda = (\log \epsilon_\lambda) - q. \quad [5]$$

In order to determine the additive relationship of structural units to the experimental integrals [5] a set of m·n sequential additive constants are determined as described in more detail hereinbelow for a chosen spectral region, where n is the number of analyzed structural units (i.e. the number of different possible monomers, nucleotides or amino acids) and m is the number of integrals [5] for the defined spectral regions. These constants must be related to the defined structural units expressed, for example, in relative molar fractions (analyzed molecule=1) and their number must equal or larger than the number of analyzed structural units. Thus we get $$Ss_\lambda = (\log \epsilon_\lambda) - q = \sum_{i=1}^{n} K_{i,\lambda} X_i, \quad [6]$$

where $Ss_\lambda$ are the experimental integrals [5] at defined wavelengths, $\lambda$, $K_{i,\lambda}$ are the corresponding additive constants for each structural unit and, $X_i$ are the molar fractions of the analyzed structural units. This results in m equations with n unknowns and n·m spectrochrome constants (where m is the number of wavelengths measured and n the number of different structural subunits). Generally, because the accuracy increases with greater m, m should be as large as possible. Suitable values for m for polymers, polynucleotides and polypeptides are described hereinbelow. When more than a necessary minimum number of constants was used (for example, 20 wavelengths for 4 nucleotides or 30 wavelengths for 25 amino acids) the equations could be treated by statistical mathematical analysis.

The polymer chains are composed of structural subunits (a) connected by a covalent bridge (b), for example, $a_1$-b-$a_1$-b-$a_1$ ... or $a_1$-b-$a_2$-b-$a_3$-b ... $a_n$. It became apparent that the number of bridges could be expressed by an additional additive logarithmic term and thus $$Ss_\lambda = (\log \epsilon_\lambda) - q = K_{n,\lambda} \cdot \log(z) + \sum_{i=1}^{n-1} K_{i,\lambda} X_i, \quad [7]$$

where z is the number of bridges (b).

Furthermore, the molecular weight of the compound may be determined because, at a known concentration, the sum $\Sigma_{i=1}^{n-1} X_i$ is equal to 1 only when the assumed molecular weight is equal to the correct molecular weight. From this the molecular weight of the studied polymer could be determined.

The sequential additive constants could be determined from standard known compounds by different mathematical methods. For polymers, these constants should be derived from known polymers of the same monomeric subunits. For polynucleotides and polypeptides, because the possible subunits are limited to those known nucleotides and amino acids, the constants may be derived from any known polynucleotides or polypeptides. In any event, the analysis of a plurality of different known standard compounds at a plurality of wavelengths, allows the determination of the values of the constants for each subunit (monomer, nucleotides or amino acid) at each wavelength, for a total of m·n constants. The calculation of these constants may be determined using known techniques for the solution of multivariable equations. For example, if two polymer standards containing different numbers of the same subunits are used, then for compound I $$K_{i,\lambda} + K_{n,\lambda} \cdot \log(z^I) = Ss_\lambda^I \quad [8]$$

and for compound II $$K_{i,\lambda} + K_{n,\lambda} \cdot \log(z^{II}) = Ss_\lambda^{II}. \quad [9]$$

From the experimental $Ss_\lambda$ of both compounds $K_{i,\lambda}$ and $K_{n,\lambda}$ may be calculated. This operation is then repeated at different wavelengths.

Similarly, three standard dimers (I–III) composed of different units, for example, $a_1$, $a_2$, $a_3$, may be used to calculate the spectrochrome constants $K_1$, $K_2$, $K_3$ at a set of suitable wavelengths from the equations $$0.5K_{1,\lambda} + 0.5K_{2,\lambda} = Ss_\lambda^I \quad [10]$$

$$0.5K_{1,\lambda} + 0.5K_{3,\lambda} = Ss_\lambda^{II} \quad [11]$$

$$0.5K_{2,\lambda} + 0.5K_{3,\lambda} = Ss_\lambda^{III}. \quad [12]$$

More standard compounds with longer chains can be treated statistically by computer programs. Without being limited thereto, one such suitable method for the determination of these spectrochrome constants by statistical analysis is described in J. Chrastil, Calculation of the Constants used for the Quantitative Determination of Molecular Weights and Composition of Polymers, Nucleotides and/or Peptides, Computers and Chemistry, 16:345–346 (1992), the contents of which are incorporated by reference herein. The skilled practitioner will recognize that the equations may also be determined using known techniques as described, for example, in Morrison, Multivariate Satistical Methods, Second Edition, McGraw Hill, New York, 1976, and in Bishop et al., Discrete Multivariate Analysis:Theory and Practice, MIT Press, Cambridge, Mass., 1975.

Examples

Organic Compounds

Purified ethyl-2-amino-α-(methoxy-imino)-4-thiazoleacetate (0.2293 mg/ml water) was transferred into a spectrophotometric cuvette of the Double Beam UV-VIS-260 Shimadzu Spectrophotometer. The spectrophotometer video monitor and its recorder showed the absorbance curve between 200 and 800 nm. The computer connected to the spectrophotometer automatically calculated the integrated spectrosum (equation 4) and printed the result $S_\Sigma = 2.6$. By comparison with the spectrochrome constants of Table 1, the experimental spectrosum 2.6 agreed well with the sum of 1 thiazole conjugated ring (1.0), 1 amino group bound to the conjugated ring (0.6), 1 C=N (0.5) and 1 C=O (0.5) groups conjugated in an aliphatic chain.

Purified bromochlorophenol blue (0.5801 mg/ml of diluted ethanol) was transferred into a spectrophotometric cuvette of the spectrophotometer of Example 1. The spectrophotometer video monitor and its recorder showed the absorbance curve between 200 and 800 nm. The computer connected to the spectrophotometer automatically calculated the integrated spectrosum (equation 4) and printed the result $S_\Sigma=6.5$. By comparison with the spectrochrome constants of Table 1 the experimental spectrosum 6.5 agreed well with the sum of 1

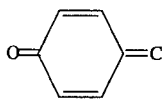

group (6.5), 2 benzene conjugated rings (1.6), 1 —OH group on aromatic (conjugated) ring (0.5), 2 —Br on aromatic (conjugated) ring (0.4), and 2 —Cl on aromatic (conjugated) ring (0.2).

Polymers

Various polymers can be studied by the sequential spectrosum method (Equation 7). For example, the molecular weights of polyethylene glycol and polyethylene oxide could be determined from the spectrosums at 191, 192, ... , 200 nm with an arbitrary constant, q=0, and the number of molecular structural subunits n=1 (ethylene).

When all additive constants are known the composition and/or the molecular weight can be calculated from the absorption spectrum of the analyzed polymer by means of Eq. [7]. The task is to solve Eqs. [7] with 10 spectrosums (at 10 wavelengths), Ss, 20 sequential additive constants, $K_{i\lambda}$, and 2 unknowns (molar fraction, $X_i$, of ethylene component and number of bridges, z). This can be done for example by a computer program, which is shown together with the additive constants for polyethylene glycol in the Appendix. Again, the skilled practitioner will recognize that the equations may be solved using known techniques for the solution of multivariable equations as described hereinabove.

Because not only the composition but also the molecular weight of an analyzed compound is unknown, the program starts with an assumed molecular weight (any molecular weight may be chosen as assumed molecular weight) and experimental absorbances at defined wavelength. Then, at first, the correct molecular weight and from this the correct sequential spectrosums are calculated by successive approximations until the sum of the molar fractions is 1. Finally, from the corrected spectrosum, the composition is calculated from the set of Eqs. [7]. A similar method was used for the polyethylene oxide. The method was checked with different pure polymer. Some examples are shown in Tables 7 to 10.

Nucleotides

The spectral region chosen for defining the sequential spectrosums of nucleotides was at 204, 208, 212, ... , 280 nm with an arbitrary constant, q=3 and the number of the molecular structural subunits, n=4 (2 purines and 2 pyrimidines).

When all additive constants are known the composition and/or the molecular weight can be calculated from the absorption spectrum of the analyzed nucleotide by means of Eq. [7]. The task is to solve Eq. [7] with 20 spectrosums (at 20 wavelengths), Ss, 100 sequential additive constants, $K_{i\lambda}$, and 5 unknowns (molar fractions, $X_i$, of A, C, G, T, or U and number of bridges, z). This can be done by a computer program, which is shown together with the additive constants for ribonucleotides and deoxyribonucleotides in the Appendix. The method was checked with different pure nucleotides. Some examples of ribonucleotides and deoxyribonucleotides are shown in Tables 11–13

Peptides

The best region for the sequential spectrosums of peptides was found to be 201, 202, . . . , 230 nm. The arbitrary constant q=1 was chosen. The number of structural subunits, n, was 24 (24 amino acids).

When all additive constants are known the composition and/or the molecular weight can be calculated from the absorption spectrum of the analyzed peptide by means of Eq. [7]. The task is to solve Eq. [7] with 30 spectrosums (at 30 wavelengths), Ss, 750 sequential additive constants, $K_{i\lambda}$, and 25 unknowns (molar fractions of amino acids, $X_i$, and number of bridges, z). Again, this can be done by a computer program, which is shown together with the additive constants for peptides in the Appendix. The method was checked with different pure peptides. Some examples are shown as computer outputs in Tables 14–17. [The calculated number of units is expressed in integers. The reliability (step 88 in the computer program) is conventionally based on the difference (expressed as a percentage) between the calculated value of the number of units (experimental errors usually make this not an integer) and the rounded integer value shown as a result (only the integer is a reasonable value for the number of units). If these two values are equal then the reliability is 100%.]

With 25 unknowns, the method is much more sensitive to impurities and to the accuracy of the absorbance values than the methods for polymers or nucleotides. The molecular weights can often be determined within 1–5% up to 50,000 Da or more with the three to four digits of absorbance accuracy, evidently because of the automatic statistical compensation of the calculated erroneous AA molecular fractions (Table 17) but the determination of the correct amino acid composition is more sensitive to absorbance. With lower-molecular-weight peptides (200–5000 DA) three to four decimal places of absorbance are sufficient, but with molecular weights above 10,000 Da, theoretically four, five or more decimal places of absorbance values are necessary for the accurate determination of amino acid composition, and this is not feasible.

The method described here is based on dimers as the smallest analyzed compounds and thus it does not work with monomers or their mixtures (including nucleic bases or amino acids). The influence of associations, hydrogen bridges, and secondary or tertiary polymer structures is often automatically included in the spectrochrome constants related to the bridges, for example, the hydrogen bridges between nucleic bases, but in some cases it could be a significant factor that might influence the composition results. Because the greatest disadvantage of this method (as with other spectrophotometric methods) is the sensitivity to impurities, the sample should be substantially pure or pure for optimal results.

General BASIC Program for Sequential Spectrochrome Analysis

For the safe of brevity, the program steps shown in the Appendix are enclosed in number marks, #, which are not parts of the program. Before using the program, the corresponding (to each category of polymers, respectively) data (Data I-V) must be inserted (appended) at steps 275–276. After insertion the program steps may be renumbered. The program calculates the molecular weight and the composition of an unknown polymer and needs the following input: number of subunits, arbitrary constant, number of wavelengths, starting wavelength, wavelength step, name, concentration (mg/liter), assumed molecular weight (any reasonable value can be used, but the assumed values that are far from the correct molecular weight require a longer calculation time), number of chains, and the experimental absorbance values at the set of wavelengths defined for each studied polymer category. The computer will print the results as shown in the examples. For other polymers (not shown here) new data files must be calculated.

If the program is to be used for other polymers (not shown here) steps 4, 80, 90–98, 253, 259, and 264–273 must be modified because they participate in the calculation of percentage and molecular weights and the numerical constants in these steps may differ from those shown in the program. Printer 1 and printer 26 are the HP-BASIC 5.0/5.1 codes for the screen and laser printer and should be modified for other computers or printers.

It is understood that the foregoing examples and detailed description are given merely by way of illustration and that variation may be made therein without departing from the spirit and scope of the invention.

TABLE 1

Additive Group Constants

| Number | Ks | Group |
|---|---|---|

I. Conjugated rings:

| 1 | 6.5 | [(R)₂N=⬡=C]; [O=⬡=C] |
| 2 | 5.5 | [O=⬡=N—OH] (with =O) |
| 3 | 4.6 | [(R)₂N=⬡—]; [O=⬡—O]; [O=⬡—S] |
| 4 | 3.0 | [O=⬡=S] |
| 5 | 2.6 | [O=⬡—]; [O=⬡=O]; [NH=⬡—]; [NH=⬡=NH]; [O=⬡—S] |

TABLE 1-continued

Additive Group Constants

| Number | Ks | Group |
|---|---|---|
| 6 | 1.5 | [O=⬡=O]; [O=C(NH—C)(NH—CO)C—] |
| 7 | 1.0 | [thiophene]; [thiazine]; [thiazole]; [thiotriazole]; [diazinone] |
| 8 | 0.8 | [benzene]; [tetraene]; [azine]; [azole]; [diazine]; [tetrazole]; [oxazole]; [furan]; [pyran] |
| 9 | 0.4 | [triazine]; [diazole][triazole]; [diazolone]; [1,4-dithiine]; [dioxatriazine] |
| 10 | 0.2 | [oxonium salts] |

II. Charged atomes in conjugated rings:

| 11 | 3.0 | [—S⁺=] |
| 12 | 1.5 | [=N⁺=]; [=N⁺—]R |

III. Groups bound to 1 conjugated ring:

| 13 | 2.5 | [(C=S]NH₂ |
| 14 | 1.9 | [N=C=S] |
| 15 | 1.8 | [C=S] |
| 16 | 1.5 | [N=N] |
| 17 | 1.2 | [NO₂] (2nd NO₂ = 0.1); [NO]OR; [NO] |
| 18 | 1.0 | [C=C]; [C=N] |
| 19 | 0.8 | [CO]R |
| 20 | 0.6 | [[NH₂]; [NHCO]R; [NHCOO]R; [SH]; [C≡C]; [C≡N] |
| 21 | 0.5 | [OH]; [CHO]; [COOH]; [COO]R; [NH]R; [OCO]R |
| 22 | 0.4 | [[S]R |
| 23 | 0.3 | [[O]R |
| 24 | 0.2 | [[N]R₂; [Br]; [I]; [NH]CONHR; [CH₂(O—)(O—)]; [pyrazolone] |
| 25 | 0.1 | [Cl]; [2nd NO₂] |
| 26 | 0.0 | [N=S]; [SO₂]; [SO₂NH]R; [NH]SO₂; [tetrazole] |

IV. Groups bound to 2 conjugated rings:

| 27 | 3.3 | [N=N] |
| 28 | 1.5 | [C=N]; [C≡] |
| 29 | 0.9 | [C=NH] |
| 30 | 0.8 | [C=O]; [C=C] |
| 31 | 0.5 | [NH] |
| 32 | 0.3 | [—C(=N)—] |
| 33 | 0.0 | [—S—]; [N=S]; [—S—S—]; [tetrazole] |

V. Groups bound to 3 conjugated rings:

| 34 | 0.6 | [C=N] |
| 35 | 0.2 | [—N—] |
| 36 | 0.0 | [N(CO)(CO)]; [—C(=N)—]; [—C(=N)—]OH |

VI. Groups bound to 4 conjugated rings:

| 37 | 0.0 | [C=C]; [=C=] |

TABLE 1-continued

Additive Group Constants

| Number | Ks | Group |
|---|---|---|
| VII. Groups conjugated in aliphatic chains or in incompletely conjugated rings. Groups bound to these rings. | | |
| 38 | .9 | [N=C=S] |
| 39 | 1.8 | [C=S]; [S—S] |
| 40 | 1.0 | [C=C; [N=N] |
| 41 | 0.8 | [CHO] |
| 42 | 0.5 | [C=O]; [C=N]; [C≡C]; [COOH]; [COO]R |
| 43 | 0.2 | [N=S]; [S]R; [S]in ring |
| 44 | 0.1 | [SH]; [O]R; [Br]; [Cl] |
| 45 | 0.0 | [OH]; [NH$_2$] |
| VIII. Non-conjugated groups: | | |
| 46 | 0.5 | [C=C]; [C=N]; [N=N]; [C=S]; [C≡C]; [NHCO]; [CO]CH$_2$CO |
| 47 | 0.3 | [C=O]; [COOH]; [COO]R |
| 48 | 0.2 | [S]; [I] |
| 49 | 0.1 | [Br]; [Cl] |
| 50 | 0.0 | [—S—S—]; [OH]; [NH$_2$]; [NH]R; [N=S] |

Note.
R is an alkyl but not an aryl;

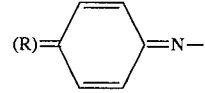

had the group constant 7.9 but it was determined with only one compound. Compounds with two or more nitrogens in aromatic ring (compounds 8 and 9) may show slight differences (±0.2) from the values shown in the table.

TABLE 2

Spectrosums of Different Compounds

| Compuond | Spectrosum Found | Calculated |
|---|---|---|
| 1 | 9.0 | 9 × 1.0(40) = 9.0 |
| 2 | 8.6 | 7 × 1.0(40) + 2 × 0.8(41) = 8.6 |
| 3 | 1.8 | 1 × 0.8(8) + 2 × 0.5(21) = 1.8 |
| 4 | 3.4 | 2 × 0.8(8) + 1 × 0.2(24) + 1 × 1.5(28) = 3.3 |
| 5 | 4.1 | 2 × 0.8(8) + 2 × 0.5(21) + 1 × 1.5(28) = 4.1 |
| 6 | 4.0 | 2 × 0.8(8) + 2 × 0.5(21) + 1 × 1.5(28) = 4.1 |
| 7 | 4.1 | 2 × 0.8(8) + 2 × 0.5(21) + 1 × 1.5(28) = 4.1 |
| 8 | 3.1 | 1 × 0.8(8) + 1 × 1.8(39) + 1 × 0.5(42) = 3.1 |
| 9 | 2.3 | 1 × 1.0(7) + 1 × 0.8(8) + 1 × 0.5(21) = 2.3 |
| 10 | 2.6 | 2 × 0.8(8) + 2 × 0.5(21) = 2.6 |
| 11 | 3.0 | 3 × 0.8(8) + 1 × 0.6(20) = 3.0 |
| 12 | 1.8 | 1 × 0.8(8) + 1 × 1.0(18) = 1.8 |
| 13 | 2.2 | 2 × 0.8(8) + 1 × 0.5(42) + 1 × 0.1(44) = 2.2 |
| 14 | 2.3 | 1 × 0.8(8) + 1 × 1.0(40) + 1 × 0.5(42) = 2.3 |
| 15 | 1.6 | 2 × 0.8(8) = 1.6 |
| 16 | 2.6 | 2 × 0.8(8) + 2 × 0.5(42) = 2.6 |
| 17 | 4.9 | 2 × 0.8(8) + 1 × 3.3(27) = 4.9 |
| 18 | 3.6 | 3 × 0.8(8) + 1 × 1.2(17) = 3.6 |
| 19 | 2.4 | 2 × 0.8(8) + 1 × 0.5(21) + 1 × 0.3(32) = 2.4 |
| 20 | 3.2 | 3 × 0.8(8) + 1 × 0.8(30) = 3.2 |
| 21 | 6.8 | 2 × 2.6(5) + 2 × 0.8(8) = 6.8 |
| 22 | 5.3 | 1 × 2.6(5) + 2 × 0.8(8) + 2 × 0.5(21) = 5.2 |
| 23 | 6.4 | 7 × 0.8(8) + 1 × 0.5(31) + 1 × 0.6(34) = 6.5 |
| 24 | 3.5 | 2 × 0.8(8) + 4 × 0.3(23) + 1 × 0.8(30) = 3.6 |
| 25 | 2.6 | 3 × 0.8 + 1 × 0.2(35) = 2.6 |
| 26 | 2.3 | 3 × 0.8(8) = 2.4 |
| 27 | 4.3 | 3 × 0.8(8) + 1 × 0.3(23) + 1 × 1.5(28) = 4.2 |
| 28 | 1.9 | 2 × 0.8(8) + 1 × 0.3(23) = 1.9 |
| 29 | 3.4 | 2 × 0.8(8) + 2 × 0.5(21) + 1 × 0.8(30) = 3.4 |
| 30 | 2.3 | 1 × 1.0(7) + 1 × 0.8(8) + 1 × 0.5(21) = 2.3 |
| 31 | 5.9 | 5 × 0.8(8) + 1 × 1.5(28) + 1 × 0.5(31) = 6.0 |
| 32 | 3.2 | 4 × 0.8(8) = 3.2 |
| 33 | 4.3 | 2 × 0.8(8) + 2 × 1.0(40) + 1 × 0.5(42) + 1 × 0.2(43) = 4.3 |
| 34 | 4.6 | 2 × 1.8(39) + 1 × 1.0(40) = 4.6 |
| 35 | 2.4 | 2 × 0.8(8) + 1 × 0.8(30) = 2.4 |
| 36 | 1.4 | 1 × 0.8(8) + 1 × 0.6(20) = 1.4 |
| 37 | 10.1 | 2 × 0.8(8) + 5 × 1.0(18) + 2 × 1.0(40) + 2 × 0.5(42) + 2 × 0.3(47) = 10.2 |
| 38 | 7.8 | 6 × 0.8(8) + 2 × 1.5(28) = 7.8 |
| 39 | 9.2 | 1 × 6.5(1) + 2 × 0.8(8) + 1 × 0.5(21) + 2 × 0.2(24) + 2 × 0.1(25) = 9.2 |
| 40 | 8.5 | 1 × 6.5(1) + 2 × 0.8(8) + 2 × 0.2(24) = 8.5 |
| 41 | 11.6 | 5 × 0.8(8) + 1 × 0.6(30) + 1 × 0.5(21) +2 2 × 3.3(27) = 11.7 |
| 42 | 3.9 | 3 × 0.8(8) + 1 × 1.5(28) = 3.9 |
| 43 | 2.0 | 1 × 0.8(8) + 1 × 0.5(21) + 1 × 0.4(22) + 1 × 0.3(47) = 2.0 |

TABLE 2-continued
Spectrosums of Different Compounds
| Compuond | Spectrosum Found | Calculated |
|---|---|---|
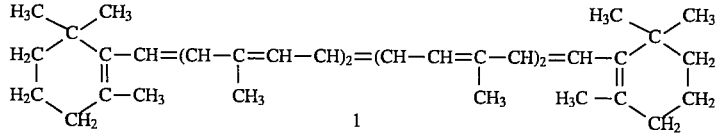
1
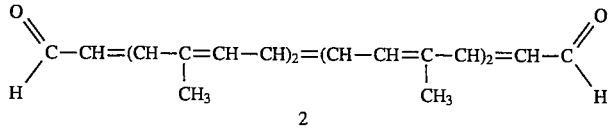
2
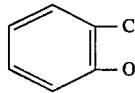
3
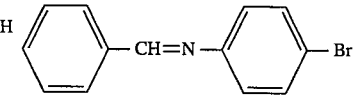
4
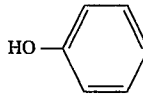
5
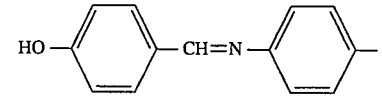
6
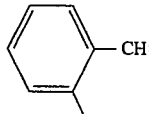
7
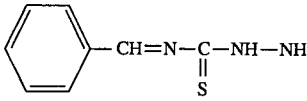
8
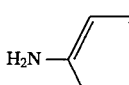
9
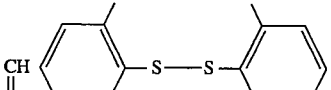
10
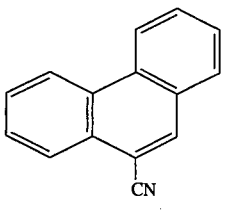
11
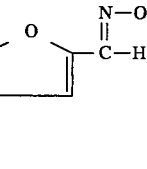
12
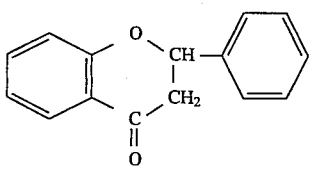
13
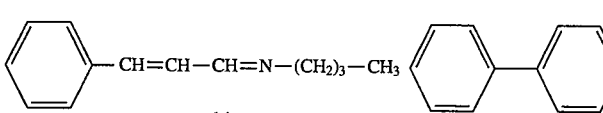
14
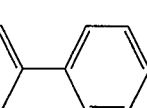
15
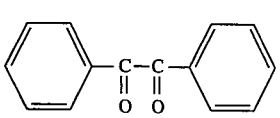
16
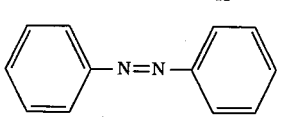
17

TABLE 2-continued
Spectrosums of Different Compounds
| Compuond | Spectrosum | |
|---|---|---|
| | Found | Calculated |
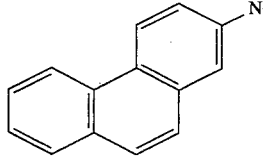
18
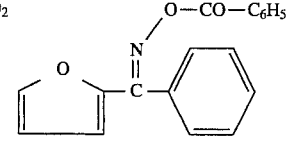
19
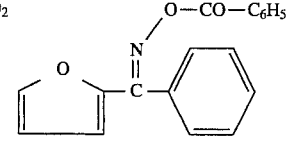
20
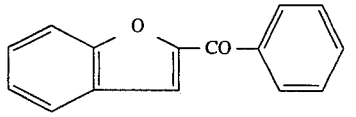
21
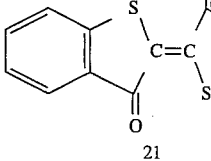
22
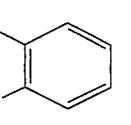
23
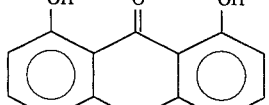
24
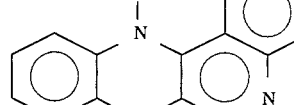
25
26
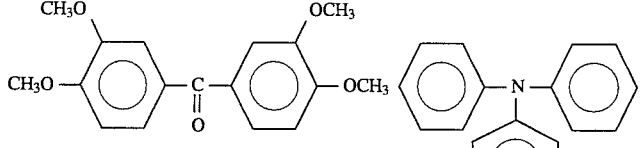
27
28
29

TABLE 2-continued
Spectrosums of Different Compounds
| Compuond | Spectrosum | |
|---|---|---|
| | Found | Calculated |
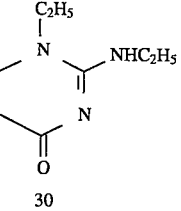

TABLE 2-continued

Spectrosums of Different Compounds

| Compuond | Spectrosum Found | Calculated |
|---|---|---|

Structures 40, 41, 41, 42, 43

TABLE 3

Tautomery of Acetylacetone Calculated from Spectrosums

| | | Percentage of C=C | |
|---|---|---|---|
| Solvent | $S_\Sigma$ | From spectrosum | From Br titration |
| Water | 1.1 | 10 | 10.5 |
| Chloroform | 1.9 | 90 | 90.5 |
| Benzene | 1.4 | 40 | 41 |
| Hexane | 1.6 | 60 | 59.5 |

Note. $S_\Sigma$ = spectrosum; acetylacetone, $10^{-5}$M; 25° C.; titration (20) of $10^{-2}$ M acetylacetone was done with 8 mg/ml Br.

TABLE 4

Tautomeric Changes of p-Nitrophenol with pH from Spectrosums

| pH | $S_\Sigma$ | % I | % II | pH | $S_\Sigma$ | % I | % II |
|---|---|---|---|---|---|---|---|
| 2.2 | 4.0 | 50 | 50 | 5.8 | 4.8 | 23 | 77 |
| 2.4 | 4.0 | 50 | 50 | 6.0 | 4.9 | 20 | 80 |
| 2.6 | 4.0 | 50 | 50 | 6.2 | 5.03 | 16 | 84 |
| 3.0 | 4.01 | 50 | 50 | 6.4 | 5.18 | 11 | 89 |
| 3.6 | 4.03 | 49 | 51 | 6.6 | 5.25 | 8 | 92 |
| 4.0 | 4.08 | 47 | 53 | 6.8 | 5.3 | 7 | 93 |
| 4.2 | 4.1 | 47 | 53 | 7.0 | 5.32 | 6 | 94 |
| 4.4 | 4.12 | 46 | 54 | 7.2 | 5.34 | 5 | 95 |
| 4.6 | 4.16 | 45 | 55 | 7.4 | 5.36 | 5 | 95 |
| 4.8 | 4.2 | 43 | 57 | 7.6 | 5.38 | 4 | 96 |
| 5.0 | 4.28 | 41 | 59 | 7.8 | 5.4 | 3 | 97 |
| 5.2 | 4.35 | 38 | 62 | 8.0 | 5.43 | 2 | 98 |
| 5.4 | 4.46 | 35 | 65 | 10 | 5.46 | 1 | 99 |
| 5.6 | 4.6 | 30 | 70 | 13 | 5.5 | 0 | 100 |

Note. See structures I and II in text; $S_\Sigma$ = spectrosum; p-nitrophenol (5 × $10^{-6}$M) was in 0.2M McIlvaine buffer at 25° C.

TABLE 5

Tautomeric Changes of Methyl Orange with pH from Spectrosums

| pH | $S_\Sigma$ | % I | % II | pH | $S_\Sigma$ | % I | % II |
|----|-----|-----|------|-----|-----|-----|------|
| 2.2 | 8.8 | 0 | 100 | 5.0 | 7.7 | 28 | 72 |
| 2.4 | 8.7 | 0 | 100 | 5.2 | 7.7 | 28 | 72 |
| 2.6 | 8.6 | 3 | 97 | 5.4 | 7.6 | 31 | 69 |
| 2.8 | 8.5 | 6 | 94 | 5.6 | 7.6 | 31 | 69 |
| 3.0 | 8.4 | 8 | 92 | 5.8 | 7.5 | 33 | 67 |
| 3.2 | 8.3 | 11 | 89 | 6.0 | 7.5 | 33 | 67 |
| 3.4 | 8.2 | 16 | 86 | 7.0 | 7.4 | 36 | 64 |
| 3.6 | 8.1 | 17 | 83 | 7.5 | 7.4 | 36 | 64 |
| 3.8 | 8.0 | 19 | 81 | 8.0 | 7.4 | 36 | 64 |
| 4.0 | 8.0 | 19 | 81 | 9.0 | 7.3 | 39 | 61 |
| 4.2 | 7.9 | 22 | 78 | 10.0 | 7.2 | 42 | 58 |
| 4.4 | 7.9 | 22 | 78 | 11.0 | 7.2 | 42 | 58 |
| 4.6 | 7.8 | 25 | 75 | 12.0 | 7.1 | 44 | 56 |
| 4.8 | 7.7 | 28 | 72 | 13.0 | 7.1 | 44 | 56 |

Note. See structures I and II in text; $S_\Sigma$ = spectrosum; methyl orange ($5 \times 10^{-6}$M) was in 0.2M McIlvaine buffer at 25° C.

TABLE 6

Tautomeric Changes of Pelargonidine with pH from Spectrosums

| pH | $S_\Sigma$ | % I | % II | pH | $S_\Sigma$ | % I | % I |
|----|-----|-----|------|-----|-----|-----|------|
| 1 | 7.2* | 0 | 100 | 5.5 | 4.7 | 96 | 4 |
| 2 | 7.0 | 8 | 92 | 6 | 4.9 | 85 | 15 |
| 2.2 | 6.8 | 15 | 85 | 6.5 | 5.7 | 58 | 42 |
| 2.4 | 6.3 | 35 | 65 | 7 | 6.7 | 19 | 81 |
| 2.6 | 5.2 | 77 | 23 | 7.5 | 7.0 | 8 | 92 |
| 2.8 | 4.9 | 85 | 15 | 8 | 7.1 | 4 | 96 |
| 3 | 4.8 | 92 | a | 9 | 7.2 | 0 | 100 |
| 3.5 | 4.7 | 96 | 4 | 10 | 7.2 | 0 | 100 |
| 4 | 4.6 | 100 | 0 | 11 | 7.2 | 0 | 100 |
| 4.5 | 4.6 | 100 | 0 | 12 | 7.2* | 0 | 100 |
| 5 | 4.6 | 100 | 0 | 13 | 7.2* | 0 | 100 |

Note. See structures I and II in text; $S_\Sigma$ = spectrosum; pelargonidine chloride ($1 \times 10^{-4}$M in 90% ethanol) was in 0.2M McIlvaine buffer at 25° C.; *; irreversible decrease to 4.4.

TABLE 7

Analysis of Polyethylene Glycol: Average $M_r = 400$ c(mg/l) = 2424 ASSUMED MW = 1000 No. of CHAINS = 1
ABSORBANCE:

| 191 nm | A = .9095 | 192 nm | A = .7904 |
|--------|-----------|--------|-----------|
| 193 nm | A = .641 | 194 nm | A = .5081 |
| 195 nm | A = .3672 | 196 nm | A = .2654 |
| 197 nm | A = .1871 | 198 nm | A = .1289 |
| 199 nm | A = .0884 | 200 nm | A = .058 |

RESULTS:

[ETG] MOL.FR. = 1  % = 100
No.of UNITS = 9  RELIABILITY = 93%
MW = 415  CONTROL ERROR = 6.3E-7

TABLE 8

Analysis of Polyethylene Glycol: Average $M_r = 8000$ c(mg/l) = 2524 ASSUMED MW = 10000 No. of CHAINS = 1
ABSORBANCE:

| 191 nm | A = .8351 | 192 nm | A = .7487 |
|--------|-----------|--------|-----------|
| 193 nm | A = .6264 | 194 nm | A = .5122 |
| 195 nm | A = .3819 | 196 nm | A = .2848 |
| 197 nm | A = .2136 | 198 nm | A = .1566 |
| 199 nm | A = .1216 | 200 nm | A = .0876 |

RESULTS:

[ETG] MOL.FR. = 1  % = 100
No.of UNITS = 181  RELIABILITY = 84%
MW = 7992  CONTROL ERROR = 1.7E-6

TABLE 9

Analysis of Polyethylene Oxide: Average $M_r = 200,000$ c(mg/l) = 2669 ASSUMED MW = 500000 No. of CHAINS = 1
ABSORBANCE:

| 191 nm | A = 1.0133 | 192 nm | A = 1.0527 |
|--------|-----------|--------|-----------|
| 193 nm | A = .9382 | 194 nm | A = .8362 |
| 195 nm | A = .701 | 196 nm | A = .6014 |
| 197 nm | A = .528 | 198 nm | A = .4635 |
| 199 nm | A = .4163 | 200 nm | A = .374 |

RESULTS:

[ETO] MOL.FR. = 1  % = 100
No.of UNITS = 4545  RELIABILITY = 27%
MW = 200209  CONTROL ERROR = 1.9E-7
RELIABILITY IS LOW! -
USE ONLY CALCULATED MW = 200195

TABLE 10

Analysis of Polyethylene Oxide: Average $M_r = 4,000,000$ c(mg/l) = 2576 ASSUMED MW = 1.E + 7
No. of CHAINS = 1
ABSORBANCE:

| 191 nm | A = .9492 | 192 nm | A = 1.0161 |
|--------|-----------|--------|-----------|
| 193 nm | A = .9056 | 194 nm | A = .8072 |
| 195 nm | A = .6567 | 196 nm | A = .5468 |
| 197 nm | A = .4658 | 198 nm | A = .3969 |
| 199 nm | A = .346 | 200 nm | A = .3016 |

RESULTS:

[ETO] MOL.FR. = 1  % = 100
No.of UNITS = 90666  RELIABILITY = 60%
MW = 3.994184E + 6  CONTROL ERROR = 2.7E-6

TABLE 11

Analysis of Ribonucleotide ApApC: $M_r = 901.6$ c(mg/l) = 28.045  ASSUMED MW = 2000  No. of CHAINS = 1
ABSORBANCE:

| 204 nm | A = 1.0859 | 208 nm | A = 1.0057 |
|--------|-----------|--------|-----------|
| 212 nm | A = .8963 | 216 nm | A = .6847 |
| 220 nm | A = .438 | 224 nm | A = .2762 |
| 228 nm | A = .2424 | 232 nm | A = .266 |
| 236 nm | A = .2987 | 240 nm | A = .3588 |

TABLE 11-continued

Analysis of Ribonucleotide ApApC: $M_r = 901.6$

| 244 nm | A = .4254 | 248 nm | A = .5037 |
|---|---|---|---|
| 252 nm | A = .5828 | 256 nm | A = .6589 |
| 260 nm | A = .69 | 264 nm | A = .6794 |
| 268 nm | A = .6149 | 272 nm | A = .4922 |
| 276 nm | A = .3621 | 280 nm | A = .2429 |
| RESULTS: | | | |
| [A] MOL. FR.= .667 | % = 68.73 | No. of UNITS = 2 | RELIABILITY = 90% |
| [C] MOL. FR. = .333 | % = 31.27 | No. of UNITS = 1 | RELIABILITY = 95% |
| [G] MOL. FR. = 0 | % = 0 | No. of UNITS = 0 | RELIABILITY = 99% |
| [U] MOL. FR. = 0 | % = 0 | No. of UNITS = 0 | RELIABILITY = 100% |

MW = 902
CONTROL ERROR = 1.7E − 5

TABLE 12

Analysis of Ribonucleotide CpCpCpG: $M_r = 1198.8$

| c(mg/l) = 28.93 | ASSUMED MW = 2000 | | No. of CHAINS = 1 |
|---|---|---|---|
| ABSORBANCE: | | | |
| 204 nm | A = 1.1984 | 208 nm | A = .9143 |
| 212 nm | A = .7305 | 216 nm | A = .5934 |
| 220 nm | A = .5223 | 224 nm | A = .5101 |
| 228 nm | A = .5857 | 232 nm | A = .6575 |
| 236 nm | A = .6541 | 240 nm | A = .6286 |
| 244 nm | A = .5866 | 248 nm | A = .5602 |
| 252 nm | A = .5667 | 256 nm | A = .5969 |
| 260 nm | A = .6178 | 264 nm | A = .6395 |
| 268 nm | A = .6544 | 272 nm | A = .6359 |
| 276 nm | A = .6038 | 280 nm | A = .5602 |
| RESULTS: | | | |
| [A] MOL. FR. = 0 | % = 0 | No. of UNITS = 0 | RELIABILITY = 100% |
| [C] MOL. FR. = .75 | % = 72.04 | No. of UNITS = 3 | RELIABILITY = 98% |
| [G] MOL. FR. = .25 | % = 27.96 | No. of UNITS = 1 | RELIABILITY = 99 |
| [U] MOL. FR. = 0 | % = 0 | No. of UNITS = 0 | RELIABILITY = 100% |

MW = 1199
CONTROL ERROR = 3.3E − 7

TABLE 13

Analysis of DNA (Calf Thymus): $M_r = 8{,}500{,}000$

| c(mg/l) = 50.025 | ASSUMED MW = 2.E + 7 | | No. of CHAINS = 1 |
|---|---|---|---|
| ABSORBANCE: | | | |
| 204 nm | A = .9463 | 208 nm | A = .8153 |
| 212 nm | A = .6847 | 216 nm | A = .53 |
| 220 nm | A = .4147 | 224 nm | A = .3349 |
| 228 nm | A = .3027 | 232 nm | A = .2883 |
| 236 nm | A = .2986 | 240 nm | A = .3519 |
| 244 nm | A = .4195 | 248 nm | A = .4944 |
| 252 nm | A = .5615 | 256 nm | A = .6138 |
| 260 nm | A = .6344 | 264 nm | A = .6279 |
| 268 nm | A = .5974 | 272 nm | A = .5226 |
| 276 nm | A = .4339 | 280 nm | A = .3363 |
| RESULTS: | | | |
| [A] MOL. FR. = .276 | % = 28.1 | No. of UNITS = 7548 | RELIABILITY = 23% |
| [C] MOL. FR. = .224 | % = 20.58 | No. of UNITS = 6111 | RELIABILITY = 92% |
| [G] MOL. FR. = .224 | % = 24.22 | No. of UNITS = 6115 | RELIABILITY = 97% |
| [T] MOL. FR. = .276 | % = 27.1 | No. of UNITS = 7551 | RELIABILITY = 30% |

MW = 8.441421E + 6
CONTROL ERROR = 5.8E − 7
RELIABILITY IS LOW! - USE ONLY CALCULATED MW = 8.4375E + 6

TABLE 14

Analysis of Glu—Gln: $M_r = 275.27$

| c(mg/l) = 46.238 | ASSUMED MW = 400 | | No. of CHAINS = 1 |
|---|---|---|---|

ABSORBANCE:

| 201 nm | A = 1.0477 | 202 nm | A = .9778 |
|---|---|---|---|
| 203 nm | A = .9125 | 204 nm | A = .8516 |
| 205 nm | A = .7857 | 206 nm | A = .7165 |
| 207 nm | A = .6535 | 208 nm | A = .596 |
| 209 nm | A = .5373 | 210 nm | A = .4789 |
| 211 nm | A = .4318 | 212 nm | A = .3893 |
| 213 nm | A = .343 | 214 nm | A = .3092 |
| 215 nm | A = .2724 | 216 nm | A = .24 |
| 217 nm | A = .2115 | 218 nm | A = .1842 |
| 219 nm | A = .1623 | 220 nm | A = .1397 |
| 221 nm | A = .1217 | 222 nm | A = .1036 |
| 223 nm | A = .0871 | 224 nm | A = .0733 |
| 225 nm | A = .0617 | 226 nm | A = .0519 |
| 227 nm | A = .0432 | 228 nm | A = .0355 |
| 229 nm | A = .0285 | 230 nm | A = .0232 |

RESULTS:

| [ALA] MOL. FR. = 0 | % = 0 | No. of AA = 0 | RELIABILITY = 100% |
|---|---|---|---|
| [ARG] MOL. FR. = 0 | % = 0 | No. of AA = 0 | RELIABILITY = 94% |
| [ASN] MOL. FR. = 0 | % = 0 | No. of AA = 0 | RELIABILITY = 100% |
| [ASP] MOL. FR. = 0 | % = 0 | No. of AA = 0 | RELIABILITY = 99% |
| [CSS] MOL. FR. = 0 | % = 0 | No. of AA = 0 | RELIABILITY = 96% |
| [CYS] MOL. FR. = 0 | % = 0 | No. of AA = 0 | RELIABILITY = 100% |
| [GLN] MOL. FR. = .5 | % = 49.81 | No. of AA = 1 | RELIABILITY = 99% |
| [GLU] MOL. FR. = .5 | % = 50.19 | No. of AA = 1 | RELIABILITY = 96% |
| [GLY] MOL. FR. = 0 | % = 0 | No. of AA = 0 | RELIABILITY = 100% |
| [HIS] MOL. FR. = 0 | % = 0 | No. of AA = 0 | RELIABILITY = 100% |
| [HYP] MOL. FR. = 0 | % = 0 | No. of AA = 0 | RELIABILITY = 100% |
| [ILE] MOL. FR. = 0 | % = 0 | No. of AA = 0 | RELIABILITY = 99% |
| [LEU] MOL. FR. = 0 | % = 0 | No. of AA = 0 | RELIABILITY = 98% |
| [LYS] MOL. FR. = 0 | % = 0 | No. of AA = 0 | RELIABILITY = 100% |
| [MET] MOL. FR. = 0 | % = 0 | No. of AA = 0 | RELIABILITY = 98% |
| [NLE] MOL. FR. = 0 | % = 0 | No. of AA = 0 | RELIABILITY = 100% |
| [NVA] MOL. FR. = 0 | % = 0 | No. of AA = 0 | RELIABILITY = 100% |
| [PHE] MOL. FR. = 0 | % = 0 | No. of AA = 0 | RELIABILITY = 99% |
| [PRO] MOL. FR. = 0 | % = 0 | No. of AA = 0 | RELIABILITY = 97% |
| [SER] MOL. FR. = 0 | % = 0 | No. of AA = 0 | RELIABILITY = 100% |
| [THR] MOL. FR. = 0 | % = 0 | No. of AA = 0 | RELIABILITY = 96% |
| [TRP] MOL. FR. = 0 | % = 0 | No. of AA = 0 | RELIABILITY = 99% |
| [TYR] MOL. FR. = 0 | % = 0 | No. of AA = 0 | RELIABILITY = 100% |
| [VAL] MOL. FR. = 0 | % = 0 | No. of AA = 0 | RELIABILITY = 100% |

MW = 275
CONTROL ERROR = 1.4E − 7

TABLE 15

Analysis of Oxidized Glutathione: $M_r = 612.64$

| c(mg/l) = 29.4 | ASSUMED MW = 1000 | | No. of CHAINS = 2 |
|---|---|---|---|

ABSORBANCE:

| 201 nm | A = 1.0015 | 202 nm | A = .9345 |
|---|---|---|---|
| 203 nm | A = .872 | 204 nm | A = .8213 |
| 205 nm | A = .7523 | 206 nm | A = .6956 |
| 207 nm | A = .6432 | 208 nm | A = .592 |
| 209 nm | A = .5349 | 210 nm | A = .4811 |
| 211 nm | A = .4428 | 212 nm | A = .3982 |
| 213 nm | A = .3549 | 214 nm | A = .3222 |
| 215 nm | A = .2885 | 216 nm | A = .2595 |
| 217 nm | A = .2345 | 218 nm | A = .208 |
| 219 nm | A = .1854 | 220 nm | A = .1676 |
| 221 nm | A = .1487 | 222 nm | A = .1319 |
| 223 nm | A = .116 | 224 nm | A = .1029 |
| 225 nm | A = .0909 | 226 nm | A = .0791 |
| 227 nm | A = .0699 | 228 nm | A = .0603 |
| 229 nm | A = .0518 | 230 nm | A = .0447 |

RESULTS:

| [ALA] MOL. FR. = 0 | % = 0 | No. of AA = 0 | RELIABILITY = 63% |
|---|---|---|---|
| [ARG] MOL. FR. = 0 | % = 0 | No. of AA = 0 | RELIABILITY = 93% |
| [ASN] MOL. FR. = 0 | % = 0 | No. of AA = 0 | RELIABILITY = 100% |
| [ASP] MOL. FR. = 0 | % = 0 | No. of AA = 0 | RELIABILITY = 91% |

TABLE 15-continued

Analysis of Oxidized Glutathione: $M_r = 612.64$

| | | | |
|---|---|---|---|
| [CSS] MOL. FR. = .2 | % = 35.43 | No. of AA = 1 | RELIABILITY = 69% |
| [CYS] MOL. FR. = 0 | % = 0 | No. of AA = 0 | RELIABILITY = 98% |
| [GLN] MOL. FR. = 0 | % = 0 | No. of AA = 0 | RELIABILITY = 89% |
| [GLU] MOL. FR. = .4 | % = 44.78 | No. of AA = 2 | RELIABILITY = 76% |
| [GLY] MOL. FR. = .4 | % = 19.79 | No. of AA = 2 | RELIABILITY = 84% |
| [HIS] MOL. FR. = 0 | % = 0 | No. of AA = 0 | RELIABILITY = 57% |
| [HYP] MOL. FR. = 0 | % = 0 | No. of AA = 0 | RELIABILITY = 86% |
| [ILE] MOL. FR. = 0 | % = 0 | No. of AA = 0 | RELIABILITY = 68% |
| [LEU] MOL. FR. = 0 | % = 0 | No. of AA = 0 | RELIABILITY = 76% |
| [LYS] MOL. FR. = 0 | % = 0 | No. of AA = 0 | RELIABILITY = 100% |
| [MET] MOL. FR. = 0 | % = 0 | No. of AA = 0 | RELIABILITY = 95% |
| [NLE] MOL. FR. = 0 | % = 0 | No. of AA = 0 | RELIABILITY = 100% |
| [NVA] MOL. FR. = 0 | % = 0 | No. of AA = 0 | RELIABILITY = 94% |
| [PHE] MOL. FR. = 0 | % = 0 | No. of AA = 0 | RELIABILITY = 93% |
| [PRO] MOL. FR. = 0 | % = 0 | No. of AA = 0 | RELIABILITY = 100% |
| [SER] MOL. FR. = 0 | % = 0 | No. of AA = 0 | RELIABILITY = 100% |
| [THR] MOL. FR. = 0 | % = 0 | No. of AA = 0 | RELIABILITY = 59% |
| [TRP] MOL. FR. = 0 | % = 0 | No. of AA = 0 | RELIABILITY = 100% |
| [TYR] MOL. FR. = 0 | % = 0 | No. of AA = 0 | RELIABILITY = 100% |
| [VAL] MOL. FR. = 0 | % = 0 | No. of AA = 0 | RELIABILITY = 80% |

MW = 613
CONTROL ERROR = 2.5E − 9

TABLE 16

Analysis of (Tyr$^4$)-bombesin: $M_r = 1688.88$
(Glu—Gln—Arg—Tyr—Gly—Asn—Gln—Trp—Ala—Val—Gly—His—Leu—Met)

c(mg/l) = 28.11    ASSUMED MW = 2000    No. of CHAINS = 1
ABSORBANCE:

| | | | |
|---|---|---|---|
| 201 nm | A = 1.0808 | 202 nm | A = .9324 |
| 203 nm | A = .8084 | 204 nm | A = .7179 |
| 205 nm | A = .6224 | 206 nm | A = .5536 |
| 207 nm | A = .4932 | 208 nm | A = .4416 |
| 209 nm | A = .3948 | 210 nm | A = .3512 |
| 211 nm | A = .3226 | 212 nm | A = .2888 |
| 213 nm | A = .2632 | 214 nm | A = .2456 |
| 215 nm | A = .2238 | 216 nm | A = .2082 |
| 217 nm | A = .1983 | 218 nm | A = .1833 |
| 219 nm | A = .1732 | 220 nm | A = .1668 |
| 221 nm | A = .1551 | 222 nm | A = .1462 |
| 223 nm | A = .1369 | 224 nm | A = .1274 |
| 225 nm | A = .1196 | 226 nm | A = .1077 |
| 227 nm | A = .0987 | 228 nm | A = .0868 |
| 229 nm | A = .0769 | 230 nm | A = .0677 |

RESULTS:

| | | | |
|---|---|---|---|
| [ALA] MOL. FR. = .071 | % = 4.25 | No. of AA = 1 | RELIABILITY = 99% |
| [ARG] MOL. FR. = .071 | % = 9.35 | No. of AA = 1 | RELIABILITY = 95% |
| [ASN] MOL. FR. = .071 | % = 6.83 | No. of AA = 1 | RELIABILITY = 81% |
| [ASP] MOL. FR. = 0 | % = 0 | No. of AA = 0 | RELIABILITY = 100% |
| [CSS] MOL. FR. = 0 | % = 0 | No. of AA = 0 | RELIABILITY = 87% |
| [CYS] MOL. FR. = 0 | % = 0 | No. of AA = 0 | RELIABILITY = 99% |
| [GLN] MOL. FR. = .143 | % = 15.34 | No. of AA = 2 | RELIABILITY = 68% |
| [GLU] MOL. FR. = .071 | % = 7.73 | No. of AA = 1 | RELIABILITY = 94% |
| [GLY] MOL. FR. = .143 | % = 6.83 | No. of AA = 2 | RELIABILITY = 93% |
| [HIS] MOL. FR. = .071 | % = 8.21 | No. of AA = 1 | RELIABILITY = 91% |
| [HYP] MOL. FR. = 0 | % = 0 | No. of AA = 0 | RELIABILITY = 100% |
| [ILE] MOL. FR. = 0 | % = 0 | No. of AA = 0 | RELIABRLITY = 100% |
| [LEU] MOL. FR. = .071 | % = 6.77 | No. of AA = 1 | RELIABILITY = 87% |
| [LYS] MOL. FR. = 0 | % = 0 | No. of AA = 0 | RELIABILITY = 100% |
| [MET] MOL. FR. = .071 | % = 7.85 | No. of AA = 1 | RELIABILITY = 92% |
| [NLE] MOL. FR. = 0 | % = 0 | No. of AA = 0 | RELIABILITY = 67% |
| [NVA] MOL. FR. = 0 | % = 0 | No. of AA = 0 | RELIABILITY = 86% |
| [PHE] MOL. FR. = 0 | % = 0 | No. of AA = 0 | RELIABILITY = 99% |
| [PRO] MOL. FR. = 0 | % = 0 | No. of AA = 0 | RELIABILITY = 100% |
| [SER] MOL. FR. = 0 | % = 0 | No. of AA = 0 | RELIABILITY = 77% |
| [THR] MOL. FR. = 0 | % = 0 | No. of AA = 0 | RELIABILITY = 100% |
| [TRP] MOL. FR. = .071 | % = 11.14 | No. of AA = 1 | RELIABILITY = 96% |
| [TYR] MOL. FR. = .071 | % = 9.77 | No. of AA = 1 | RELIABILITY = 98% |
| [VAL] MOL. FR. = .071 | % = 5.93 | No. of AA = 1 | RELIABILITY = 87% |

MW = 1689
CONTROL ERROR = 2.8E − 8

TABLE 17

Determinations of Molecular Weights of Some Higher-Molecular-Weight Peptides

| Peptide (%) | $M_r$ (from sequence) | Calculated $M_r$ | Difference |
| --- | --- | --- | --- |
| Lysozyme | 14,306 | 14,766 | +3.2 |
| Ribonuclease A | 13,746 | 14,090 | +3.5 |
| Chymotrypsinogen A | 25,655 | 24,853 | −3.1 |
| Oryzenin (acid subunit) | 32,037 | 31,348 | −2.2 |
| Oryzenin (basic subunit) | 22,168 | 22,097 | −0.3 |
| Albumin (bovine) | 66,494 | 68,952 | +3.7 |

Note. Three peptide samples were used with different dilutions at different wavelength ranges (201–210, 211–220, and 221–230 nm) in triplicate. In this manner the absorbance could be determined for each wavelength as an average with four significant digits.

APPENDIX 1

```
#1#DIM C(30),D(25),E(25),I1(25),J1(25),S(25),T(25,26),X(30,26),Y(25),
Z$(28)[80]#2#DIM Mf(25),Na(25),Pr(25),Sh(25),Er(25)#3#printer is
1#4#INPUT "INPUT 1 FOR PEG; 2 FOR PEO;3 FOR NUCLEOTIDES: 4 FOR
PEPTIDES",Zz#5#INPUT"No. OF UNITS=",N,"ARBITRARY CONSTANT Q =",Bb
#6#INPUT "No. OF WAVELENGTHS =",Mm,"STARTING WAVELENGTH =",N2,"STEP
(nm) =",A1#7#PRINT "No. OF UNITS =;"N;" ARBITRARY CONSTANT Q =";Bb
#8#PRINT "No. OF WAVELEGTHS =";Mm;" STARTING WAVELENGTH =";N2;"STEP
(nm) =";A1#9#N=N+1#10#Nn=1#11#Mw1=0#12#N3=N2−A1#13#N4=0#14#Uuu=1#15#R
ESTORE#16#FOR I=1 TO N−1#17#READ Z$(I)#18#NEXT I#19#FOR I=1 TO N−1
#20#READ E(I)#21#NEXT I#22#FOR Q=1 TO Mm#23#FOR J=1 TO N#24#READ Z
#25#X(Q,J)=Z#26#NEXT J#27#NEXT Q#28#printer is 1#29#INPUT "NAME",
Z$(N+1),"c(mg/l)",Ww,"MW ASSUMED",Mw,"No. OF CHAINS",Ii#30# PRINTER
IS 26#31#PRINT Z$(N+1)#32#PRINT "c(mg/l) =";Ww;" ASSUMED MW =";Mw;"
No. OF CHAINS =";Ii#33#PRINT#34#PRINT"ABSORBANCE:"#35#PRINT#36#
PRINTER IS 1#37#Uu=Mw#38#PRINT "INPUT ABSORBANCE FROM";N2; "nm To THE
LAST WAVELENGTH"#39#FOR I=1 TO Mm#40#INPUT "ABSORBANCE", Ab#41#PRINT
Ab#42#C(I)=Ab#43#X(I,N+1)=LGT(C(I)*Mw*1000/Ww)−Bb#44#Ss=.00001*INT(X(
I,N+1)*100000+.5)#45#NEXT I#46#FOR I=1 TO Mm#47#IF FRACT (I/2)=0 THEN
52#48#PRINT N3+A1*I;"nm";TAB(10);"A =";C(I);TAB(30);N3+A1*I+A1;"nm";
TAB(40);"A =";C(I+1)#49#PRINTER IS 26#50#PRINT N3+A1*I;"nm";TAB(10);
"A =";C(I);TAB(30); N3+A1*I+A1;"nm";TAB(40);"A =";C(I+1)#51#PRINTER IS
1#52#NEXT I#53#IF Nn=1 THEN 56#54#PRINT "MW LOOP-WAIT"#55#GOTO 57#56#
PRINT "ALL A INSERTED-WAIT"#57#FOR I=1 TO Mm#58#X(I,N+1)=LGT(C(I)*Mw*
1000/Ww)−Bb#59#NEXT I#60#FOR I=1 TO N#61#FOR J=1 To N+1#62#T(I,J)=0
#63#NEXT J#64#NEXT I#65#FOR Q=1 TO Mm#66#FOR I=1 TO N#67#FOR J=1 TO
N+1#68#T(I,J)=T(I,J)+X(Q,I)*X(Q,J) #69#NEXT J#70#NEXT I#71#NEXT Q
#72#GOSUB 157#73#GOTO 119#74#PRINTER IS 26#75#PRINT#76#PRINT "RE-
SULTS:"#77#PRINT#78#IF S(N)<0 THEN S(n)=0 #79#Kkk=10^S(N)+Ii#80#IF
Zz< >4 THEN 85#81#IF S(5)<0 THEN S(5)=0#82#Na(5)=S(5)*Kkk/(1+S(5))
#83#Fff=Kkk−Na(5)#84#GOTO 86#85#Fff=Kkk#86#GOSUB 246#87#FOR I=1 TO
N−1#88#Er(I)=INT(100−200*ABS(S(I)*Fff−Na(I)))#89#IF Er(I)<50 THEN
N4=9#90#IF Zz=2 THEN 94#91#IF Zz=1 THEN 94#92#IF Zz=3 THEN 98#93#IF
I=5 THEN 96#94#Pr(I)=.01*INT((E(I)−18.016)*Na(I)*10000/(Ee-Aa*18.016)
+.5)#95#GOTO 99#96#Pr(I)=.01*INT((E(I)−36.032)*Na(I)*10000/(Ee-Aa*18.
016)+.5)#97#GOTO 99#98#Pr(I)=.01*INT(E(I)*Na(I)*10000/Ee+.5)#99#
PRINTER IS 1#100#PRINT Z$(I);"MOL. FR.=";Mf(I);TAB(22):"%=";Pr(I);
TAB(35);"No. OF UNITS=";Na(I);TAB(55);"RELIABILITY=";Er(I);"%"#101#
PRINTER IS 26#102#PRINT Z$(I);"MOL. FR.=";Mf(I);TAB(22);"%=";Pr(I);
TAB(35);"No. OF UNITS=";Na(I);TAB(55);"RELIABILITY=";Er(I);"%"#103#
PRINTER IS 1#104#NEXT I#105#GOSUB 237#106#PRINT "MW =";INT(Mwf +.5);"
CONTROL ERROR =";ABS(DROUND(A0,2))#107#PRINT #108#IF N4=0 THEN 110
#109#PRINT "RELIABILITY IS LOW!- USE ONLY CALCULATED MW =";INT
(Mw+.5)#110#PRINTER IS 26#111#PRINT#112#PRINT "MW =";INT(Mwf+.5);"
CONTROL ERROR =";ABS(DROUND(A0,2))#113#PRINT #114#IF N4=0 THEN 116
#115#PRINT "RELIABILITY IS LOW! - USE ONLY CALCULATED MW =";INT
(Mw+.5)#116#INPUT #INPUT y FOR ANOTHER COMPOUND OR n FOR GOTO START"
,Z$(N+3)#117#IF Z$(N+3)="y" THEN 10#118#GOTO 1#119#Qq=0#120#IF Zzz=9
THEN 125#121#FOR I=1 TO N−1#122#Qq=Qq+S(I)#123#NEXT I#124#GOTO 128
#125#FOR I=1 TO N−1#126#Qq=Qq+1/S(I)#127#NEXT I#128#PRINTER IS 1
#129#PRINT "MW (ASSUMED)=":INT(Mw+.5)#130#PRINT "CONTROL INDEX=";
.000001*INT(Qq*1000000+.5)#131#IF (Qq<1.0001) AND (Qq>.9999) THEN
154#132#IF (Nn=1) AND (Qq<1) THEN Mw=Mw*2#133#IF Uuu=1 THEN Qqq1=Qq
#134#IF Uuu=1 THEN Mww1=Mw#135#IF Uuu=2 THEN Qqq2=Qq#136#IF Uuu=2
THEN Mww2=Mw#137#Uuu=Uuu+1#138#If (Uuu=3) AND (Qqq2<Qqq1) AND
(Mww2>Mww1) THEN Zzz=9#139#If(Uuu=3) AND (Qqq2>Qqq1) AND (Mww2<Mww1)
THEN Zzz=9#140#IF (Nn=1) AND (Qq<1) THEN 54#141#IF Qq>1 THEN Uu=Mw
#142#IF Qq>1 THEN Mw=(Mw+Mw1)/2#143#IF Qq<1 THEN Mw1=Mw#144#IF Qq<1
THEN Mw=(Uu+Mw1)/2#145#Nn=2#146#IF Uuu=1 THEN Qqq1=Qq#147#IF Uuu=1
THEN Mww1=Mw#148#IF Uuu=2 THEN Qqq2=Qq#149#IF Uuu=2 THEN Mww2=Mw
#150#Uuu=Uuu+1#151#IF (Uuu=3) AND (Qqq2<Qqq1) AND (Mww2>Mww1) THEN
Zzz=9#152#IF (Uuu=3) AND (Qqq2>Qqq1) AND (Mww2<Mww1) THEN Zzz=9
```

APPENDIX 1-continued

153#GOTO 53#154#PRINTER IS 1#155#PRINT "MW (ASSUMED)=";INT (Mw+.5)
156#GOTO 74#157#M=N+1#158#F=1#159#FOR K=1 TO N#160#B=K-1 #161#P=0
162#FOR I=1 TO N#163#FOR J=1 TO N#164#IF K=1 THEN 171 #165#FOR G=1
TO B#166#FOR R=1 TO B#167#IF I=I1(G) THEN 175#168#IF J=J1(R) THEN
175#169#NEXT R#170#NEXT G#171#IF ABS(T(I,J))<=ABS(P) THEN 175#172#
P=T(I,J)#173#I1(K)=I#174#J1(K)=J#175#NEXT J#176#NEXT I #177#IF
ABS(P)>1.E-100 THEN 180#178#F=0#179#RETURN#180#H=I1(K)#181#U=J1(K)
182#F=F*P#183#FOR J=1 TO M#184#T(H,J)=T(H,J)/P#185#NEXT J#186#T(H,U)
=1/P#187#FOR I=1 TO N#188#O=T(I,U)#189#IF I=H THEN 194#190#T(I,U)=-
O/P#191#FOR J=1 TO M#192#IF J< >U THEN T(I,J)=T(I,J)-O*T(H,J)#193#NEXT
J#194#NEXT I#195#NEXT K#196#FOR I=1 TO N#197#L=I1(I)#198#V=J1(I)#199#
D(L)=V#200#S(V)=T(L,M)#201#Sh(V)=S(V)#202#NEXT I#203#O=0#204#N1=N-
1#205#FOR I=1 TO N1#206#P1=I+1#207#FOR J=P1 TO N#208#IF D(J)>=D(I)
THEN 213#209#W=D(J)#210#D(J)=D(I)#211#D(I)=W#212#O=O+1#213#NEXT J
214#NEXT I#215#IF INT(O/2)*2< >O THEN F=-F#216#FOR J=1 TO N#217#FOR
I=1 TO N#218#L=I1(I)#219#V=J1(I)#220#Y(V)=T(L,J)#221#NEXT I#222#FOR
I=1 TO N#223#T(I,J)=Y(I)#224#NEXT I#225#NEXT J#226#FOR I=1 TO N#227#
FOR J=1 TO N#228#L=I1(J)#229#V=J1(J)#230#Y(L)=T(I,V)#231#NEXT J#232#
FOR J=1 TO N#233#T(I,J)=Y(J)#234#NEXT J#235#NEXT I#236#RETURN#237#
A0=0#238#FOR I=1 TO Mm#239#O=0#240#FOR J=1 TO N#241#O=O+X(I,J)*Sh(J)
242#NEXT J#243#A0=A0+X(I,N+1)-O#244#NEXT I#245#RETURN#246#Aa=0#247#
Ee=0#248#FOR I=1 TO N-1#249#IF S(I)<0 THEN S(I)=0#250#Na(I)=INT(S(I)
*Ff+.5)#251#IF Na(I)<1 THEN 257#252#Ee=Ee+E(I)*Na(I)#253#IF Zz< >4
THEN 256#254#IF I=5 THEN Aa=Aa+2*Na(I)#255#IF I=5 THEN 257#256#Aa=
Aa+Na(I)#257#NEXT I#258#FOR I=1 TO N-1#259#IF Zz< >4 THEN 262#260#
Mf(I)=.001 *INT(10000*Na(I)/(Aa-Na(5))+.5)#261#GOTO 263#262#Mf(I)=
.001*INT(1000*Na(I)/Aa+.5)#263#NEXT I#264#IF Zz=2 THEN 273#265#IF
Zz=1 THEN 271#266#IF Zz=3 THEN 269#267#Mwf=Ee-(Aa-Ii)*18.016#268#GOTO
274#269#Mwf=Ee+(Aa-Ii)*61.97#270#GOTO 274#271#Mwf=Ee+(Aa-Ii)*16+
34.015#272#GOTO 274#273#Mwf=Ee+(Aa-Ii)*16#274#RETURN#275#DATA [INSERT
DATA!]#276#END
DATA for polyethylene glycols.
5000 DATA [ETG],28.054
5010 DATA 1.37,0.91,1.30,0.92,1.20,0.93,1.09,0.94,0.94,0.95,0.79,0.96,0.62,0.98
5020 DATA 0.44,1.00,0.24,1.04,0.03,1.07
5030 END
DATA for polyethylene oxides.
5000 DATA [ETO],28.054
5010 DATA 1.26,0.99,1.24,1.00,1.19,1.00,1.14,1.00,1.10,0.99,1.07,0.98,1.05,0.97
5020 DATA 1.03,0.96,1.02,0.95,1.01,0.94
5030 END
DATA for ribonucleotides.
5000 DATA [A],[C],[G],[U],267.24,243.22,283.24,244.20
5010 DATA 1.26,1.26,1.21,0.96,0.94,1.27,1.14,1.10,0.95,0.94,1.23,1.07,0.92,0.91
5020 DATA 0.94,1.08,1.01,0.72,0.81,0.95,0.79,0.99,0.52,0.67,0.97,0.48,1.00,0.43
5030 DATA 0.49,0.98,0.37,1.05,0.52,0.34,0.98,0.43,1.06,0.71,0.32,0.97,0.54,1.00
5040 DATA 0.90,0.43,0.96,0.69,0.94,1.03,0.57,0.95,0.84,0.87,1.12,0.70,0.95,0.97
5050 DATA 0.83,1.16,0.82,0.95,1.06,0.84,1.15,0.90,0.95,1.12,0.88,1.12,0.96,0.95
5060 DATA 1.13,0.92,1.06,0.99,0.95,1.10,0.96,1.00,0.98,0.95,1.02,0.99,0.95,0.94
5070 DATA 0.95,0.88,0.98,0.93,0.86,0.95,0.69,0.96,0.90,0.74,0.95,0.45,0.92,0.89
5080 DATA 0.55,0.95
5090 END
DATA for deoxyribonucleotides.
5000 DATA [A],[C],[G],[T],251.24,227.22,267.24,242.23
5010 DATA 1.24,1.23,1.19,1.02,0.91,1.24,1.11,1.07,0.98,0.91,1.20,1.04,0.90,0.94
5020 DATA 0.91,1.05,1.00,0.69,0.89,0.91,0.77,0.96,0.50,0.81,0.92,0.46,0.98,0.41
5030 DATA 0.68,0.93,0.35,1.04,0.50,0.51,0.93,0.40,1.04,0.69,0.39,0.92,0.52,0.98
5040 DATA 0.88,0.38,0.91,0.66,0.91,1.01,0.45,0.91,0.81,0.85,1.09,0.56,0.91,0.94
5050 DATA 0.82,1.13,0.68,0.91,1.04,0.82,1.13,0.78,0.91,1.10,0.85,1.10,0.86,0.91
5060 DATA 1.11,0.90,1.04,0.91,0.91,1.08,0.94,0.98,0.94,0.91,1.00,0.97,0.94,0.95
5070 DATA 0.91,0.86,0.95,0.91,0.92,0.91,0.67,0.93,0.89,0.85,0.91,0.42,0.89,0.88
5080 DATA 0.74,0.91
5090 END
DATA for peptides.
5000 DATA [ALA],[ARG],[ASN],[ASP],[CSS],[CYS],[GLN],[GLU],[GLY],[HIS],[HYP]
5010 DATA [ILE], [LEU], [LYS], [MET], [NLE], [NVA],[PHE], [PRO], [SER], [THR], [TRP]
5020 DATA [TYR],[VAL],89.09,174.20,132.12,133.10,240.30,121.16,146.15,147.13
5030 DATA 75.05,155.16,131.13,131.17,131.17,146.19,149.21,131.17,117.15,165.19
5040 DATA 115.13,105.09,119.12,204.22,181.19,117.15
5050 DATA 2.70,3.11,2.78,2.75,3.34,3.59,2.80,2.79,2.74,3.16,2.98,2.80,2.81,2.73
5060 DATA 2.96,2.69,2.79,3.17,3.04,2.75,2.80,4.02,3.79,2.79,0.73,2.68,3.05,2.73
5070 DATA 2.73,3.36,3.60,2.76,2.77,2.72,3.16,2.99,2.78,2.79,2.71,2.94,2.67,2.76
5080 DATA 3.18,3.08,2.73,2.79,4.03,3.68,2.77,0.70,2.65,2.98,2.69,2.71,3.38,3.61
5090 DATA 2.72,2.75,2.70,3.17,3.00,2.75,2.78,2.68,2.93,2.64,2.73,3.18,3.11,2.70
5100 DATA 2.77,4.04,3.58,2.75,0.67,2.62,2.92,2.64,2.69,3.39,3.60,2.68,2.73,2.68
5110 DATA 3.18,3.00,2.73,2.75,2.65,2.91,2.61,2.70,3.20,3.14,2.67,2.74,4.06,3.49
5120 DATA 2.73,0.65,2.59,2.86,2.59,2.66,3.41,3.57,2.64,2.70,2.65,3.19,3.01,2.71
5130 DATA 2.72,2.61,2.90,2.58,2.67,3.20,3.17,2.64,2.71,4.09,3.43,2.70,0.62,2.55
5140 DATA 2.79,2.54,2.64,3.42,3.54,2.59,2.67,2.62,3.21,3.01,2.68,2.70,2.58,2.88

APPENDIX 1-continued

```
5150 DATA 2.54,2.63,3.19,3.20,2.60,2.68,4.13,3.39,2.67,0.60,2.51,2.72,2.49,2.61
5160 DATA 3.43,3.50,2.54,2.64,2.59,3.22,3.01,2.65,2.67,2.54,2.86,2.50,2.60,3.18
5170 DATA 3.22,2.55,2.65,4.18,3.36,2.65,0.58,2.47,2.67,2.44,2.57,3.43,3.45,2.49
5180 DATA 2.61,2.56,3.24,3.01,2.62,2.64,2.50,2.83,2.45,2.56,3.16,3.24,2.13,2.62
5190 DATA 4.23,3.35,2.62,0.56,2.43,2.61,2.39,2.54,3.43,3.39,2.44,2.57,2.52,3.26
5200 DATA 3.00,2.59,2.60,2.46,2.81,2.40,2.51,3.14,3.26,2.47,2.58,4.30,3.35,2.59
5210 DATA 0.54,2.39,2.55,2.34,2.50,3.42,3.34,2.38,2.53,2.48,3.27,2.99,2.56,2.57
5220 DATA 2.42,2.78,2.35,2.47,3.11,3.28,2.42,2.54,4.37,3.36,2.55,0.52,2.34,2.49
5230 DATA 2.28,2.46,3.41,3.28,2.33,2.49,2.45,3.29,2.98,2.52,2.53,2.37,2.75,2.30
5240 DATA 2.42,3.06,3.29,2.36,2.50,4.44,3.38,2.52,0.51,2.29,2.43,2.23,2.42,3.40
5250 DATA 3.22,2.28,2.45,2.41,3.31,2.97,2.49,2.49,2.32,2.72,2.24,2.37,3.00,3.30
5260 DATA 2.31,2.46,4.52,3.41,2.48,0.49,2.24,2.38,2.18,2.38,3.38,3.17,2.22,2.40
5270 DATA 2.36,3.33,2.95,2.45,2.45,2.28,2.68,2.19,2.32,2.94,3.31,2.26,2.41,4.60
5280 DATA 3.44,2.44,0.48,2.18,2.30,2.12,2.33,3.35,3.11,2.17,2.36,2.31,3.34,2.93
5290 DATA 2.41,2.40,2.22,2.65,2.13,2.26,2.87,3.32,2.20,2.36,4.69,3.48,2.40,0.48
5300 DATA 2.13,2.24,2.07,2.28,3.32,3.07,2.11,2.31,2.27,3.35,2.90,2.36,2.35,2.16
5310 DATA 2.60,2.06,2.21,2.79,3.32,2.13,2.31,4.77,3.53,2.36,0.47,2.07,2.18,2.01
5320 DATA 2.22,3.29,3.05,2.05,2.26,2.22,3.36,2.87,2.31,2.30,2.10,2.56,1.99,2.15
5330 DATA 2.71,3.32,2.07,2.26,4.84,3.59,2.32,0.47,2.02,2.11,1.95,2.17,3.26,3.04
5340 DATA 1.99,2.21,2.16,3.37,2.84,2.26,2.25,2.05,2.52,1.92,2.09,2.61,3.32,2.01
5350 DATA 2.21,4.92,3.66,2.27,0.48,1.96,2.05,1.90,2.11,3.22,3.04,1.93,2.15,2.11
5360 DATA 3.36,2.80,2.21,2.20,1.98,2.47,1.84,2.03,2.52,3.31,1.94,2.15,4.98,3.73
5370 DATA 2.22,0.48,1.90,1.98,1.84,2.06,3.16,3.05,1.87,2.10,2.05,3.35,2.75,2.15
5380 DATA 2.15,1.91,2.42,1.76,1.97,2.41,3.30,1.88,2.09,5.04,3.81,2.17,0.49,1.84
5390 DATA 1.92,1.78,2.00,3.10,3.06,1.80,2.04,2.00,3.34,2.71,2.09,2.09,1.85,2.37
5400 DATA 1.68,1.90,2.31,3.28,1.81,2.03,5.09,3.88,2.11,0.51,1.78,1.85,1.71,1.93
5410 DATA 3.05,3.08,1.73,1.99,1.93,3.32,2.66,2.02,2.03,1.77,2.32,1.60,1.84,2.19
5420 DATA 3.26,1.73,1.97,5.12,3.96,2.06,0.52,1.71,1.78,1.64,1.86,2.97,3.11,1.65
5430 DATA 1.93,1.87,3.30,2.60,1.95,1.96,1.69,2.27,1.50,1.76,2.07,3.24,1.65,1.89
5440 DATA 5.14,4.03,1.99,0.54,1.65,1.71,1.56,1.79,2.89,3.14,1.57,1.86,1.81,3.26
5450 DATA 2.53,1.87,1.90,1.62,2.20,1.40,1.69,1.96,3.20,1.56,1.81,5.15,4.10,1.93
5460 DATA 0.56,1.59,1.64,1.49,1.72,2.81,3.17,1.48,1.80,1.75,3.22,2.46,1.78,1.83
5470 DATA 1.53,2.15,1.29,1.61,1.86,3.16,1.46,1.72,5.13,4.16,1.86,0.58,1.52,1.57
5480 DATA 1.40,1.65,2.71,3.21,1.39,1.74,1.68,3.16,2.39,1.69,1.76,1.44,2.09,1.19
5490 DATA 1.53,1.77,3.12,1.37,1.63,5.10,4.21,1.79,0.61,1.45,1.47,1.32,1.57,2.61
5500 DATA 3.25,1.30,1.68,1.61,3.09,2.30,1.60,1.68,1.34,2.02,1.08,1.45,1.68,3.07
5510 DATA 1.27,1.54,5.04,4.25,1.71,0.63,1.39,1.39,1.23,1.49,2.51,3.30,1.20,1.62
5520 DATA 1.54,3.01,2.21,1.49,1.61,1.23,1.96,0.96,1.36,1.61,3.01,1.15,1.43,4.95
5530 DATA 4.27,1.62,0.66,1.32,1.29,1.13,1.40,2.39,3.36,1.10,1.55,1.48,2.91,2.13
5540 DATA 1.38,1.53,1.13,1.90,0.84,1.28,1.54,2.96,1.03,1.33,4.84,4.28,1.53,0.68
5550 DATA 1.25,1.19,1.03,1.34,2.25,3.42,0.98,1.48,1.41,2.79,2.03,1.25,1.45,1.02
5560 DATA 1.83,0.72,1.21,1.47,2.89,0.90,1.21,4.72,4.27,1.44,0.71,1.17,1.09,0.94
5570 DATA 1.26,2.12,3.49,0.87,1.41,1.34,2.66,1.92,1.14,1.36,0.90,1.77,0.59,1.12
5580 DATA 1.41,2.83,0.76,1.10,4.60,4.24,1.33,0.74
5590 END
```

I claim:

1. A method for determining one or both of the structure or molecular weight of a chemical compound selected from the group consisting of organic compounds, polymers, polynucleotides and polypeptides, comprising:

(a) providing a sample of said chemical compound in a spectrophotometer;

(b) passing a light beam at a first wavelength $\lambda_l$ within the UV or visible spectra from said spectrophotometer through said sample;

(c) measuring the absorbance of said sample at $\lambda_l$;

(d) repeating steps (b) and (c) at a plurality of different wavelengths from $\lambda_l$ to $\lambda_m$ within the UV or visible spectra and wherein m is an integer greater than one, to measure the absorbance of said sample at each said wavelength;

(e) determining the spectrosum from the absorbance measured in (c) and (d);

(f) determining one or both of the structure or molecular weight of said chemical compound from said spectrosum;

wherein said spectrosum is determined as $$S_\Sigma = \int_{\lambda_l}^{\lambda_m} f_\lambda(\log \epsilon - q) d\lambda$$

wherein $S_\Sigma$ is the spectrosum, $\epsilon$ is the extinction coefficient, and q is an arbitrary constant.

2. A method as described in claim 1 wherein said chemical compound is dissolved in a solvent.

3. A method as described in claim 2 wherein said solvent is selected from the group consisting of water, alcohols, buffers, acids and alkali.

4. A method as described in claim 1 wherein said chemical compound is an organic compound.

5. A method as described in claim 4 wherein $\lambda_l$ is about 200 nm and $\lambda_m$ is about 800 nm.

6. A method as described in claim 1 wherein said chemical compound is a polymer, polynucleotide or polypeptide.

7. A method as described in claim 1 wherein said sample of said compound is substantially pure.

8. A method as described in claim 1 wherein said sample of said compound is pure.

* * * * *